United States Patent [19]

Rieder et al.

[11] 4,425,599

[45] Jan. 10, 1984

[54] CAVITY ILLUMINATING DEVICE

[75] Inventors: Peter Rieder, Dietikon; Robert Schürmann, Meilen, both of Switzerland

[73] Assignee: Volpi AG, Urdorf, Switzerland

[21] Appl. No.: 384,200

[22] Filed: Jun. 3, 1982

[30] Foreign Application Priority Data

Jun. 5, 1981 [CH] Switzerland .................. 3710/81

[51] Int. Cl.³ .............................................. F21V 7/04
[52] U.S. Cl. ...................................... 362/32; 362/277;
362/280; 362/282; 362/293; 362/294; 362/307;
362/319; 362/321; 362/322
[58] Field of Search ................. 362/32, 277, 280, 282,
362/293, 294, 307, 319, 321, 322

[56] References Cited

U.S. PATENT DOCUMENTS 4,233,650  11/1980  Hagner et al. ..................... 362/322
4,366,529  12/1982  Takahashi et al. .................. 362/321

Primary Examiner—Stephen J. Lechert, Jr.
Attorney, Agent, or Firm—Anthony H. Handal

[57] ABSTRACT

An improved device for controlled illumination of a cavity such as in endoscopy or inspection of machinery within a housing; the device comprises a light source and a fiber optics for feeding light into the cavity, and a control means arranged between the light source and the entrance plane of the fiber optics for controlling the luminous density at the exit plane of the fiber optics; the control means is in the form of a diaphragm disc arranged between the light source and the entrance plane of the fiber optics and is capable of linear or rotational displacement or motion; the disc has an opening having a width that varies cross-wise to the direction of displacement or motion of the disc-shaped diaphragm so as to provide a variable aperture; the luminous density at the exit plane will, in general, be determined by the light flux that impinges upon the entry plane, and that flux is controlled by the variable aperture.

14 Claims, 2 Drawing Figures

CAVITY ILLUMINATING DEVICE

BACKGROUND OF THE INVENTION

The present invention generally relates to fiber optics and specifically to controlled illumination of a cavity by means of a light source and a fiber optics for feeding light from said source into the cavity and having a control means between said light source and the entrance plane of the fiber optics for controlling the luminous density at the exit plane of the fiber optics.

Devices of the type just described are used, among other purposes, in connection with mirror systems or instruments for inspection of cavities. A well known example of such an instrument is the endoscope used in the medical art for direct inspection of body organs or for technological use in the inspection of inaccessible inner spaces of cavities of machines and the like. Preferably, such illuminating devices also include a heat eliminating means, such as a filter arranged between the light source and the entrance of the fiber optics so as to prevent that heat radiation enters into the fiber optics. Consequently, such illuminating devices are sometimes referred to as "cold-light sources."

Various means are known to influence illumination of a cavity by means of the luminous density at the exit end of the fiber optics. For example, the luminous density or light-flux from the light source can be controlled by means of changing the feeding current or voltage of the electric light source or by changing the effective phase section of the feeding current. However, this will change the color temperature of the light source and thus the color of the illuminated object; such color change is particularly disadvantageous if the image of the mirror instrument is to be photographed or transmitted or recorded by video techniques. Further, for illumination control, a neutral or gray wedge, Goldberg wedge, wedge filter or the like absorptive device can be arranged in the optical path between the light source and the entrance of the fiber optics. The range of varying luminous densities by means of a gray wedge is limited, however, and a gray wedge or the like does not permit unobstructed permeation of light but will always reduce maximum illumination of the cavity. Further, a conventional optical diaphragm can be used but this has disadvantages as well. For example, an iris diaphragm will change the entrance angle of the light into the fiber optics and the exit angle of the light emanating from the fiber optices; sectored diaphragms or fan-fading diaphragms have the disadvantage that at least one diaphragm sector will remain in the light path even at maximum aperture and thus will reduce, as does the gray wedge, the maximum illumination of the cavity that would otherwise be possible with the specific light source and light transmission capacity of the system used.

SUMMARY OF THE INVENTION

Thus, it is an object of the present invention to provide for a device for controlled and variable illumination of a cavity in which the light flux from the light source is not diminished at full aperture and wherein a change of illumination will cause neither a change of the color temperature of the light source nor of the aperture angle of the light beam entering into the fiber optics or emanating therefrom.

Another object is a cold-light source with improved light flux control.

Another object is an improved method of controlling luminous density in fiber optics.

Further objects will become apparent as the specification proceeds.

Now according to a first general embodiment, the invention provides for an improved device for controlled illumination of a cavity comprising a light source; the inventive device includes a fiber optics for feeding light from a light source into a cavity; the fiber optics has an entrance plane near the light source and an exit plane remote from the light source; further, the device includes means for controlling luminous density at the exit plane of the fiber optic means between the light source and the entrance plane of the fiber optic means; the control according to the invention includes a disc-shaped diaphragm and a means connected with the diaphragm for controlled displacement of motion thereof in a plane defined essentially by the disc, that plane being substantially vertical to a light beam from the light source to the entrance plane; the diaphragm is provided with an opening having a longitudinal dimension or length and a cross-longitudinal dimension or width; the cross-longitudinal or transverse dimension varies along the longitudinal dimension, generally in an essentially gradual manner; and controlled displacement or motion of the disc is effected in a general direction that coincides essentially with the longitudinal dimension of the opening so that an aperture of varying width is provided between the light source and the entrance plane when the means for controlled displacement or motion of the diaphragm is operated.

Thus, the above object is met according to the invention by providing an illuminating device of the type defined above with the characteristic feature that the effective aperture of the diaphragm is defined by the position of the opening of the disc-shaped diaphragm relative to the path of light between light source and entry plane of the fiber optics.

The device according to the invention provides for the advantage that the light impinging upon the entrance plane of the fiber optics can be varied continuously without change of color temperature, and without a change of the light entry angle, and without reducing the maximum light flux possible with the light source.

According to a second general embodiment, the invention provides for an improved method of controlling luminous density at an exit plane of a fiber optic means by controlling the light flux from a light source to an entrance plane of said fiber optics; the improvement resides essentially in providing a displaceable or rotatable diaphragm disc between the light source and the entrance plane substantially vertical to the beam and having an elongated opening with a width (cross-longitudinal or transverse dimension) that varies over its length (longitudinal dimension) and has a maximum size that is at least as great as the largest surface dimension of the entrance plane; the light flux to the entrance plane is controlled by moving the disc into a position where the width of the opening determines the portion of the light beam which impinges upon the entrance plane.

DEFINITION OF TERMS

The term "disc" as used herein generally refers to a planar structure of an opaque solid material having a thickness dimension that is small in relation to both length and width of the structure.

The term "diaphragm" refers to optical devices of the type used in the path of a beam of light for controlling the light flux thereof; the terms "disc-shaped diaphragm" and "diaphragm disc" are used interchangeably herein and refer to diaphragms of the type where the disc as defined above has an "opening" serving as an "aperture" in the optical sense when positioned in an optical path.

The terms "fiber optics" and "fiber optic means" as used herein are intended to typically refer to flexible optical conductors comprising a multiplicity of light conductive fibers, e.g. glass fibers, in the form of a bundle or strand; generally, the bundle includes an adhesive, matrix or the like for interconnection of the fibers, and a sheath, sleeve or the like is arranged around the fiber bundle; the bundle ends are arranged in planes, generally by grinding vertically to the axes of the fibers; when used for illumination of a cavity, one of the planes is arranged near a light source and referred to as "entrance plane" while the other plane is placed near the site that is to be illuminated and is referred to as the "exit plane."

The term "mixed fiber bundle" is used herein to refer to irregular or random positioning of the fiber ends in one end plane relative to the fiber ends in the other end plane; thus, an optical image projected onto one end of a mixed fiber bundle will not appear at the other bundle end as the same image, or not as an image at all but as a diffuse luminosity because of the change of relative positions of fiber ends from one end to the other. Use of a fiber optics with a more or less random distribution of the fibers at each end of the bundle is preferred for many purposes of the invention because a substantially uniform luminous density can be achieved at the exit plane of the fiber optics even if the fibers at the entrance plane of the fiber optics are illuminated inhomogeneously, image-wise or in part only.

The term "cold-light" as used herein refers to light, or a light beam, which contains only a negligible amount of heat radiation, e.g. only very little radiation in the infrared range of the spectrum, if any.

BRIEF DISCUSSION OF PREFERRED EMBODIMENTS

According to a first preferred embodiment, the cross-longitudinal dimension or width of the opening increases from one end to another end thereof (in longitudinal direction).

According to another preferred embodiment, the opening has a substantially symmetrical shape with the line of symmetry of that shape extending length-wise over the opening and, even more preferred, running parallel to the direction of controlled disc displacement.

The symmetrical shape can be that of a substantially straight wedge or, more preferred, that of a curved wedge, i.e. a so-called "sickle-blade" shape.

Preferably, with a straight wedge opening, the line of symmetry is a substantially straight line and the line of diaphragm displacement is parallel with the straight line.

By the same token, with a curved wedge or sickle-shape opening, the preferred disc displacement is around a disc center, e.g. displacement of the opening along the line of symmetry of the sickle-shaped opening.

For many purposes it is preferred that the entrance plane of the fiber optic means has a substantially circular shape and that the opening of the diaphragm has a maximum width that is at least as great and preferably greater than the diameter of the entrance plane; in general, the luminous density at the exit plane of the fiber optics will be proportional with the illumination of the entrance plane.

Preferably, the device comprises means associated with the light source, e.g. adjacent the source, in the optical path between the light source and the entrance plane of the fiber optics, such as a selective reflector ("cold-light mirror") or a selective light absorber, such as a filter, for removing heat radiation.

Generally, fiber optics of the mixed fiber bundle type are preferred for many purposes.

BRIEF DESCRIPTION OF THE DRAWINGS

An embodiment of the novel device will be explained with reference to the accompanying drawings in which.

DETAILED DESCRIPTION OF THE INVENTION

Figure 1:
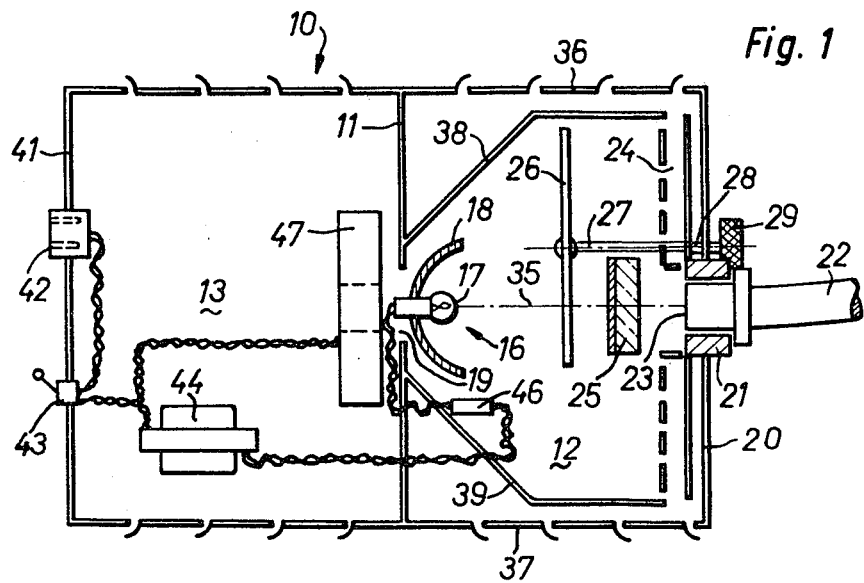
FIG. 1 is a diagrammatic top view of the novel illuminating device and FIG. 2 is the top view of a diaphragm disc with a sickle-shaped opening.

FIG. 1 is a diagram of the top view of an illuminating device in which the cover or top lid has been removed. The device comprises a housing 10 that is subdivided by a partition wall 11 into two chambers 12, 13. A light source 16 is arranged in the first chamber 12 adjacent the center of partitioning wall 11. Light source 16 includes a glass bulb 17 including an incandescent wire and is associated with a cold-light mirror 18 which is non-reflective for heat radiation. The socket of the light source is mounted in an opening 19 of partitioning wall 11. The diameter of that opening is substantially greater than the diameter of the socket of the lamp so as to permit passage of a gaseous coolant such as air.

A connector piece our coupling 21 for holding a fiber optics 22 is mounted on front wall 20 of housing 10 substantially opposite lamp 16. Fiber optics 22 is held in coupling 21 in a conventional manner, e.g. by means of a thread, a plug connection or a bayonet-type fitting. A director 24 for guiding coolant air is arranged adjacent the inner side of front wall 20 and near entrance plane 23 of fiber optics 22. Further, an interference filter 25 is mounted in front of entrance plane 23 of fiber optics 22 and has a coating for reflecting infrared radiation at the surface near light source 16. Cold-light mirror 18 near light source 16 as well as interference filter 25 reduce the amount of infrared radiation in the light impinging upon fiber optics 22 and being transmitted by the latter. Primarily, such reduction of infrared radiation is intended to prevent heating of the fiber optics because extended heat impact might soften the adhesive between the individual fibers of the bundle so as to adversely influence or destroy the fiber optics.

Figure 2:
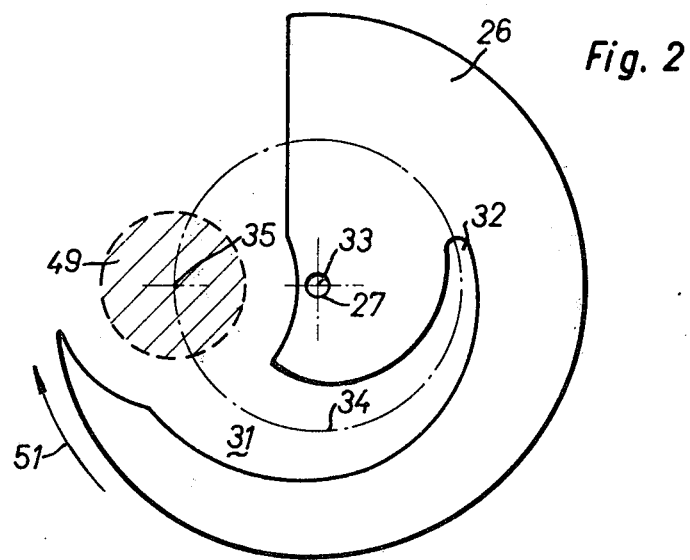

As is apparent from FIG. 2, diaphragm 26 is arranged in the path of light beam 49 having a beam axis 35 between light source 16 and interference filter 24. Diaphragm 26 is a circular disc mounted on a rotatable axis or shaft 27. Rotatable shaft 27 is supported by a bearing 28 in the front wall of the housing, and a control knob 29 or button is mounted at the free end of the shaft for manual operation of the diaphragm disc. Such operation serves to control displacement of disc 26 by rotating motion until the desired portion of opening 31 that is to define the aperture is in operative position as explained below.

As apparent from FIG. 2, diaphragm disc 26 is provided with a sickle-shaped opening or slot 31 extending from a very narrow inner end or apex portion 32 symmetrically with regard to symmetry line 34 that extends around center 33 in a circular arc. The distance of symmetry line 34 from center 33 of diaphragm disc 26 corresponds to the distance of shaft 27 of diaphragm disc 26 from axis 35 of the light beam that is directed from light source 16 towards entrance plane 23 of fiber optics 22.

Side walls 36, 37 of chamber 12 are provided with air-passing slots; light source 16, diaphragm disc 26 and filter 25 are enclosed by two guide walls 38, 39 for defining the stream of coolant air generated in chamber 11 by a blower 47.

A plug or socket 42 for connecting the illuminating device with a source of electrical power, e.g. an electrical mains connection and a switch 43, are provided in back wall 41 of second chamber 13. Transformer 44 is arranged in second chamber 13 and the secondary winding of transformer 44 provides the operating current for light source 16. Second chamber 13 further includes tangential blower 47 adjacent the opening 19 in partitioning wall 11. For protecting light source 16 against overheating, the electrical connection or lead between transformer 44 and light source 16 passes through a portion of first chamber 12 where a thermally activated cut-out switch 46 is arranged in the immediate vicinity of light source 16.

It will be understood that by suitable selection of the shape of the sickle-shaped opening 31 in diaphragm disc 26, a linear or logarithmic or other type of dependence of the luminous density at the exit plane of fiber optics 22 upon the angular position of diaphragm disc 26 will be obtained.

When using the novel device according to the invention, light radiating from the incandescent wire of bulb 17 will be transformed by cold-light mirror 18 into a substantially parallel light beam 49 impinging upon entrance plane 23 of fiber optics 22. As mentioned above, the infrared portion of the light produced by the light source will, at least predominantly, be removed by selective reflection of mirror 18 and extinguished by interference filter 25 so that the light entering into fiber optics 22 at plane 23 contains substantially no heat radiation.

Further, the cross-sectional area of light beam 49 impinging upon entrance plane 23 of fiber optics 22 can be varied by displacement of diaphragm disc 26 so as to vary the aperture-effective width of the curved wedge or sickle-shaped opening 31.

When using a diaphragm disc having the shape and opening illustrated in FIG. 2, and when the beam produced by the light source has the cross-section 49 shown in broken line, rotational displacement of diaphragm disc 26 in the direction of arrow 51 will diminish the cross-section of the light beam in horizontal direction while remaining unchanged in vertical direction. As a consequence, the density of illumination or light flux at entrance plane 23 of fiber optics 22 will be diminished while the entry angle of the light beam with reduced cross-sectional area will remain unchanged in at least one direction.

As mentioned above, when using a fiber optics of the mixed fiber type, the mutual position of the ends of the individual fibers is different at the entrance and exit sides of the fiber optics. As a consequence, fiber ends arranged adjacent to each other at the entrance plane in an illuminated or darkened portion will be randomly distributed at the exit side or plane of the fiber optics so that the exit plane will not show light and shadow portions that are macroscopically distinguishable, but will have a substantially uniform density of illumination over its entire area.

It will be appreciated that suitable elements for the inventive device except the diaphragm can be obtained commercially, including fiber optics, connectors, light sources, selective reflectors and filters for heat radiation, blowers, transformers and the other circuitry elements mentioned above, so that a more detailed discussion is not required. Further, commercially available combinations of elements may be used, e.g. a commercial cold-light source of the type including an incandescent lamp with associated cold-light mirror (reflective for light in blue portion of visible range but non-reflective for infrared portion), such as the cold-light mirror lamp obtainable from General Electric Company (Type DDL 150 W/20 V). Halogen lamps, i.e. incandescent lamps containing small amounts of gaseous halogen in the reduced-pressure atmosphere within the glass bulb around an incandescent wire made of tungsten, are suitable for many purposes.

Commercially available fiber optics with as few as 50 fibers per bundle or as many as 62,000 fibers per bundle have been used in tests with the inventive device, and have been found to be suitable.

Diaphragm discs suitable for the inventive device can be made of opaque sheet materials from a variety of diverse materials, such as cardboard, wood, pigmented plastics, metal sheet and the like. The method used for producing the opening may depend upon the material but punching, sawing and the like are typical.

Suitable displacement control devices depend upon the type of motion suitable in view of the shape of the opening: with the preferred curved wedge or sickle-blade shaped opening, displacement is by rotation and an example for control has been given above (shaft plus turning knob); a generally round or circular shape of the disc will be suitable in that connection but is not critical.

With a "straight" wedge-type shape of the disc opening (i.e. line of symmetry is a straight line but wedge sides may be straight or curved) and for linear motion, preferably in a direction of the symmetry line, a rectangular shape of the disc may be advantageous as it provides for simple displacement guidance and control, e.g. betwee slide rails or rolls including stops or the like for manual operation, e.g. by sliding the disc back and forth along the symmetry line of the wedge.

EXAMPLE

The light source used was a commercial halogen lamp with cold-light mirror as explained above in an arrangement substantially as set forth in the drawings.

The diameter of diaphragm disc 26 was 90 mm; the diameter of circular symmetry line 34 of the sickle-shaped opening was 50 mm. The sickle-shaped opening extended over an angle of about 180° and increased from a smallest width of 2 mm at apex 32 to a maximum width of 20 mm, measured transversely to the symmetry line. Two conventional fiber optics 22 used in the device had a diameter of 13 mm and comprised 62,000 glass fibers each having a diameter of 50 micrometers, and 32,000 glass fibers each having a diameter of 70 micrometers, respectively. Two other fiber optics 22 used in the device had a diameter of only 0.5 mm and comprised 95 glass fibers each having a diameter of 50 micrometers, or 50 glass fibers each having a diameter of 70 micrometers, respectively.

Coolant air (ambient temperature) entering through air entry slots in side walls 36, 37 of first chamber 12 was guided by walls 38, 39 to the external entry side of the coolant distributor device 24 and passed over entrance plane 23 of fiber optics 22 and filter 25 to light source 16. At this point, the coolent air has taken up a substantial amount of heat and is drawn-off through opening 19 in partitioning wall 11 by tangential blower 47 into second chamber 13 and passes from second chamber 13 through the ventilation slots in the chamber walls into the environment.

Thus, it is seen that the invention, in a first general and preferred embodiment thereof, provides for an illumination device including a slideable or rotatable disc-shaped diaphragm between a light source and the entrance plane of a fiber optics, said disc being moveable transversely to the direction of the light beam from the light source; the opening of disc preferably is shaped in the manner of a wedge or a sickle-blade. As a consequence of the varying width of the opening, linear or circular motion of the disc will cause that a varying portion of the light beam is retained or stopped by the diaphragm so that the intensity of illumination at the entrance and the luminous density at the exit planes of the fiber optics will be controlled correspondingly.

By using fiber optics of the mixed fiber type, a uniform luminous density can be obtained at the exit plane of the fiber optics even when the entrance plane is not uniformly illuminated; use of means associated with the light source and eliminating a portion, at least, of the heat radiation produced by the source is preferred to prevent undesirable heating of the fiber optics and/or the cavity that is illuminated.

Various modifications of the above disclosed specific embodiments of the invention will be readily apparent to those skilled in the art. It is the applicant's intention to cover by their claims all those changes and modifications which could be made to the embodiments of the invention herein chosen for the purpose of the disclosure without departing from the spirit and scope of the invention.

Protection by Letters Patent of this invention in all its aspects as the same are set forth in the appended claims is sought to the broadest extent that the prior art allows.

Accordingly,

What we claim is:

1. In a device for controlled illumination of a cavity comprising a light source; a fiber optic means for feeding light from said light source into said cavity, said fiber optic means having an entrance plane near said light source and an exit plane remote from said light source; and control means for controlling luminous density at said exit plane of said fiber optic means, said control means being arranged between said light source and said entrance plane of said fiber optic means; said control means comprising a disc-shaped diaphragm and a means connected with said diaphragm for controlled displacement thereof in a plane defined essentially by said disc shape, said plane being substantially vertical to a light beam from said light source to said entrance plane; said diaphragm being provided with an opening having a longitudinal dimension and a cross-longitudinal dimension, said cross-longitudinal dimension varying along said longitudinal dimension; and a direction of said controlled displacement coinciding essentially with said longitudinal dimension of said opening for providing an aperture of varying width between said light source and said entrance plane and controlling the change of illumination without changing the color temperature of said light source when said means for controlled displacement of said diaphragm is operated.

2. The device of claim 1 wherein said cross-longitudinal dimension of said opening increases from one end thereof in said longitudinal direction to another end thereof in said longitudinal direction.

3. The device of claim 2 wherein said opening has a substantially symmetrical shape with a line of symmetry of said shape extending in the direction of said longitudinal dimension.

4. The device of claim 3 wherein said symmetrical shape is substantially that of a straight wedge.

5. The device of claim 4 wherein said line of symmetry is a substantially straight line.

6. The device of claim 5 wherein the direction of said controlled displacement of said diaphragm is parallel to said straight line.

7. The device of claim 3 wherein said line of symmetry is defined by a curve in form of a section of a circle and wherein said symmetrical shape of said opening is essentially that of a curved wedge or sickle-blade.

8. The device of claim 7 wherein the direction of said controlled displacement of said diaphragm is parallel to said curve.

9. The device of claim 1 wherein said controlled displacement is a circular motion of said diaphragm disc around a center thereof, and wherein said longitudinal dimension of said opening extends along a portion of a circle around said center of said diaphragm disc.

10. The device of claim 1 wherein said entrance plane of said fiber optic means has a substantially circular diameter, said opening of said diaphragm having a maximum width that is at least as great as said circular diameter of said entrance plane, and wherein the luminous density at said exit plane of said fiber optics is proportional with the illumination at said entrance plane.

11. The device of claim 1 comprising means associated with said light source for eliminating a heat radiation portion thereof.

12. The device of claim 11 wherein said associated means are selected from the group consisting of selective reflectors and filters.

13. The device of claim 1 wherein said fiber organic means comprises a bundle of fibers wherein the relative positions of the fiber ends at the entrance plane are at random variance with the relative positions of the fiber ends at the exit plane.

14. In the method of controlling luminous density at an exit plane of a fiber optic means by controlling the light flux from a light source to an entrance plane of said fiber optic means the improvement consisting essentially in providing a rotatable diaphragm disc between said light source and said entrance plane substantially vertical to said beam and having an elongated opening with a width that varies over its length and has a maximum size that is at least as great as a largest surface dimension of said entrance plane, and controlling said light flux to said entrance plane without changing the color temperature of said light source by moving said disc into a position where said width of said opening determines that portion of said beam which impinge upon said entrance plane.

* * * * *